(12) United States Patent
Heesch

(10) Patent No.: US 9,283,347 B2
(45) Date of Patent: Mar. 15, 2016

(54) DEVICE FOR DISPENSING OXYGEN FOR AN ANESTHESIA DEVICE

(75) Inventor: Ralf Heesch, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 824 days.

(21) Appl. No.: 13/530,785

(22) Filed: Jun. 22, 2012

(65) Prior Publication Data

US 2012/0325208 A1 Dec. 27, 2012

(30) Foreign Application Priority Data

Jun. 25, 2011 (DE) .................... 20 2011 102 318 U

(51) Int. Cl.
 *A61M 16/10* (2006.01)
 *A61M 16/18* (2006.01)

(52) U.S. Cl.
 CPC .......... *A61M 16/104* (2013.01); *A61M 16/1015* (2014.02); *A61M 16/18* (2013.01); *A61M 2202/0208* (2013.01); *A61M 2202/0283* (2013.01); *A61M 2205/502* (2013.01)

(58) Field of Classification Search
 CPC ............ A61M 16/01; A61M 16/1015; A61M 16/1035; A61M 16/104; A61M 16/18; A61M 16/201; A61M 16/202
 See application file for complete search history.

(56) References Cited

U.S. PATENT DOCUMENTS

| | | | |
|---|---|---|---|
| 2,778,223 A | 1/1957 | Kimbrell | |
| 3,521,634 A | 7/1970 | Goodyear et al. | |
| 4,313,436 A * | 2/1982 | Schwanbom et al. | ... 128/203.12 |
| 4,345,612 A * | 8/1982 | Koni et al. | ............... 137/101.19 |
| 4,442,856 A * | 4/1984 | Betz | .................................. 137/98 |
| 4,611,590 A * | 9/1986 | Ryschka et al. | ......... 128/203.14 |
| 4,657,710 A | 4/1987 | Smith et al. | |
| 4,738,283 A | 4/1988 | Shirai et al. | |
| 4,798,689 A * | 1/1989 | Heim et al. | .................. 261/39.1 |
| 4,972,831 A * | 11/1990 | von dem Hagen et al. | ........................ 128/204.21 |
| 4,991,576 A * | 2/1991 | Henkin et al. | ........... 128/203.28 |
| 5,049,317 A | 9/1991 | Kiske et al. | |
| 5,237,990 A * | 8/1993 | Psaros et al. | ............. 128/204.21 |
| 5,398,675 A * | 3/1995 | Henkin et al. | ............ 128/203.12 |
| 5,509,406 A | 4/1996 | Kock et al. | |
| 5,687,709 A * | 11/1997 | Akerberg | ................. 128/203.12 |
| 5,694,924 A * | 12/1997 | Cewers | .................... 128/204.21 |
| 5,697,364 A | 12/1997 | Chua et al. | |
| 6,024,087 A * | 2/2000 | Kersey et al. | ............. 128/203.12 |
| 6,250,302 B1 | 6/2001 | Rantala | |
| 6,776,158 B1 * | 8/2004 | Anderson et al. | ........ 128/203.12 |
| 7,438,072 B2 | 10/2008 | Izuchukwu | |
| 2003/0140922 A1 | 7/2003 | Dunlop | |

(Continued)

FOREIGN PATENT DOCUMENTS

| | | |
|---|---|---|
| CN | 87103348 A | 12/1987 |
| CN | 1246372 A | 3/2000 |

(Continued)

*Primary Examiner* — Justine Yu
*Assistant Examiner* — LaToya M Louis
(74) *Attorney, Agent, or Firm* — McGlew and Tuttle, P.C.

(57) ABSTRACT

A device (10) for dispensing oxygen for an anesthesia device includes a switching element (15) that diverts oxygen between a first gas path (153) and a second gas path (154). The first gas path (153) leads to a patient (27) via a connection and port element. The second gas path (154) leads to a gas tapping port (20) for oxygen or gas insufflation.

18 Claims, 2 Drawing Sheets

(56) References Cited

U.S. PATENT DOCUMENTS

| | | | |
|---|---|---|---|
| 2006/0207593 A1* | 9/2006 | Dittmann et al. | 128/203.12 |
| 2010/0175695 A1* | 7/2010 | Jamison | 128/203.14 |
| 2011/0088694 A1* | 4/2011 | Tobia et al. | 128/204.23 |

FOREIGN PATENT DOCUMENTS

| | | |
|---|---|---|
| CN | 101469925 A | 7/2009 |
| CN | 101518664 A | 9/2009 |
| CN | 201308700 Y | 9/2009 |
| DE | 29 45 575 A1 | 5/1981 |
| DE | 39 24 123 A1 | 1/1991 |
| DE | 199 07 362 A1 | 8/2000 |
| DE | 695 15 391 T2 | 12/2000 |
| DE | 10 2005 012 340 B3 | 5/2006 |
| EP | 0 684 049 B1 | 7/1999 |
| EP | 0 916 358 B1 | 3/2005 |
| JP | 7323089 A | 12/1995 |

\* cited by examiner

DEVICE FOR DISPENSING OXYGEN FOR AN ANESTHESIA DEVICE

CROSS REFERENCE TO RELATED APPLICATIONS

This application claims the benefit of priority under 35 U.S.C. §119 of German Utility Model 20 2011 102 318.8 filed Jun. 25, 2011, the entire contents of which are incorporated herein by reference.

FIELD OF THE INVENTION

The present invention pertains to a device for dispensing oxygen to an anesthesia device.

BACKGROUND OF THE INVENTION

Anesthesia devices are used in anesthesia in order to maintain the patient in a pain-free and unconscious state during a surgery. These anesthesia devices comprise essentially gas-mixing units, a respiration drive, as well as feed lines leading to the patient. Various gases, e.g., oxygen, air and nitrous oxide, are sent to the gas-mixing unit. Another dispensing element in an anesthesia device is an anesthetic evaporator, by which anesthetics are added into the gas, which is then sent to the patient via feed lines.

DE 199 07 362 A1 shows a device for mixing at least one first and one second gas component by means of a Venturi nozzle, with a propellant gas port for propellant gas, a suction duct and a gas outlet. To improve the ratio of the gas components to be mixed relative to one another, a first bypass line deflecting a first partial flow of the first gas component to the suction duct with a first throttling point is provided between the propellant gas port and the suction duct.

DE 695 15 391 T2 describes an anesthesia system with a fresh gas source, wherein a defined inflow of fresh breathing gas into a breathing circuit is controlled on the basis of a rate of flow detected by a flow meter. The anesthesia system is designed such that the flow meter can be calibrated, while the system is being operated, so that a supply of fresh breathing gas into the breathing circuit is made possible continuously or essentially continuously.

U.S. Pat. No. 7,438,072 B2 describes a portable anesthesia device with a mixing system for mixing gases, with an anesthetic evaporator, with an inlet and outlet for carrier gases, wherein the gas flow and the mixing of gases are controlled by means of a control and control means such that an essentially constant anesthetic gas concentration is obtained in the gas flow to the patient.

CN 201308700 Y shows a portable anesthesia device with a pressure-reducing valve, wherein the pressure-reducing valve is connected to a pressurized oxygen cylinder that is under high pressure. A pressure-measuring unit and a flow meter unit are present. The oxygen is fed to a patient via an anesthetic evaporator and a mask.

DE 10 2005 012 340 B3 shows an anesthesia system with an anesthetic evaporator. In DE 10 2005 012 340 B1, a valve is located upstream of the anesthetic evaporator, so that the gas flow is sent completely or partly through the anesthetic evaporator or a bypass line during operation as intended, whereas the gas flows exclusively through the anesthetic evaporator in case of an error.

U.S. Pat. No. 4,657,710 A shows an anesthetic evaporator with an electronically controlled valve, by which a carrier gas is split into a first gas path and a second gas path, wherein the gas is enriched with a volatile anesthetic in the second gas path before it flows again into the first gas path.

DE 39 24 123 A1 and the corresponding U.S. Pat. No. 5,049,317 A show a dispensing device for gas mixtures with an anesthetic evaporator and with controllable adjusting elements, as a result of which a gas mixture flows to the patient either through a bypass line past the anesthetic evaporator and thus bridges over the anesthetic evaporator, or the gas mixture flows to and through the anesthetic evaporator to the patient by means of an evaporator line. A calibration volume with a filling level display is provided, into which opens a calibrating line, which can be separated from the evaporator line by shut-off elements. Manual or automatic calibration of the gas mixture flow meter unit is possible as a result, especially for small quantities of gas, without an interruption of the measurement of the quantity of gas being necessary.

Various dispensing systems are present at an anesthesia device for respirating and supplying the patient during and after surgery. A surgery with anesthesia of a patient can be divided into three essential time periods. There is an induction phase, a surgery phase and the phase of reversal of anesthesia or recovery phase. A quantity of gas with volatile anesthetics is typically fed to the patient by means of a mask during the induction phase, so that the patient is unconscious and free from pain. It is then possible to insert the endotracheal tube into him, with which the surgery phase proper will then start and the patient is respirated and anesthetized in the intubated state. The patient is supplied again with fresh gas via the mask during the reversal or recovery phase after removal of the endotracheal tube. The fresh gas used during the recovery phase is preferably provided with an oxygen concentration higher than the normal concentration of 21% in ambient air, so that the patient can recover his own breathing activity quite rapidly due to the increased oxygen supply. For this induction phase as well as for the reversal phase, the gas is not fed to the patient via the mixer, which mixes together the gases into a gas mixture consisting of nitrous oxide, air and oxygen during the surgery, but another, additionally present gas supply means, the so-called oxygen insufflation gas supply means is selected, by means of which oxygen can be fed to the patient as a gas at a separate port additionally and independently, besides the normal gas dispensing branch. This gas flows through the anesthetic evaporator and then reaches, enriched with anesthetic, the port for the oxygen insufflation unit and the patient via a breathing tube. The gas mixture is controlled by the mixer automatically during and under a surgery according to the settings selected by the user. The mixer is designed to mix oxygen, air and nitrous oxide with one another to form a gas mixture. The user decides during the induction how much anesthetic he adds at the anesthetic evaporator via an adjusting element. There is no active flow through the anesthetic evaporator during the recovery, so that pure oxygen is made available to the patient. This oxygen insufflation takes place in the dispensing unit via a separate control valve with a corresponding display. A so-called flow tube combined with a control valve is commonly used for this in the state of the art.

The flow tube is a floating-body flow meter, as it is described, for example, in U.S. Pat. No. 2,778,223 A. A floating body is floating in this case in a tube and moving up and down vertically at a scale and the user can dispense via the control valve and see directly how much oxygen is being dispensed from the level to which the floating body rose. The oxygen insufflation unit thus makes it possible to supply the patient with oxygen via a mask placed on the patient's face before and after the surgery. Such a device for oxygen insufflation is shown in U.S. Pat. No. 5,697,364 A1.

In addition to providing gas to the patient via the mixer and by means of the oxygen insufflation unit, there is another way to dispense oxygen to the patient. This way extends, entirely independently, besides and past any dispensing unit, directly from the oxygen admission via a switching element, the so-called $O_2$ flush button, directly to the patient without flow through the anesthetic evaporator. Anesthetic and nitrous oxide are flushed completely out of the system by means of an oxygen blast triggered by the user by means of the $O_2$ flush button. However, this $O_2$ flush is not suitable for being used for oxygen insufflation, because the volume and pressure are released to the patient in an uncontrolled manner only by manually operating the button. U.S. Pat. No. 3,521,634 A shows an anesthesia device with a housing, in which a chamber is arranged for receiving a volatile anesthetic, a pressurized gas source, as well as adjustable valves and gas lines, in which anesthesia device such an $O_2$ flush functionality is contained.

Another way of dispensing oxygen at an anesthesia system is the so-called emergency gas supply. This emergency gas supply is necessary for the anesthetist to be able, in case of failure of the mixer or in case of failure of the electric power supply, to continue the anesthesia by means of a manual oxygen dispensing unit, in practice in the form of a labeled adjusting wheel, with which a volume flow of oxygen is dispensed, and by means of the flow through the anesthetic evaporator, the so-called vapor. The anesthetist now takes over the manual respiration of the patient by means of a manual breathing bag.

An emergency oxygen gas supply unit for an anesthesia device is shown in EP 0 916 358 B1. The state of failure of the general gas supply and mixing of gases is recognized by continuously monitoring the flow through the gas-mixing valves. If the failure of a valve is recognized from a deviation from a set point, operation is immediately switched over to supplying the patient with oxygen by means of a bypass line, where manual means for dispensing the flow as well as for displaying the dispensed quantity flowing through may be additionally provided in the bypass line.

EP 0 684 049 B1 describes a manually actuated safety valve for a respirator or anesthesia device. The valve is designed to allow two different volume flows to flow through the valve from an inlet duct to an outlet duct at two different working points in addition to the closed state.

U.S. Pat. No. 6,250,302 B1 shows a process and a device in conjunction with a respirator, wherein the gas is supplied via a gas mixer for a plurality of possible applications for respirating a patient. A gas mixture is fed to the patient via a movable piston, with a quantity of fresh gas flowing into the piston via a gas mixer.

Thus, the types of dispensing oxygen and gases to the patient with an anesthesia device are described in the state of the art.

These four ways are present essentially independently from each other. Gas dispensing for the operation during the surgery via the gas mixer for mixing oxygen, nitrous oxide and air with subsequent flow through the anesthetic evaporator is the essential controlled way of carrying out the anesthesia. The emergency gas supply is designed for the case of failure of the mixer or of the electric power supply to enable the anesthetist to continue the anesthesia even without the mixer or additional electric systems in the anesthesia device functioning. The oxygen insufflation unit, which is used especially during induction and reversal, is designed to bring oxygen directly to the patient via an additional branch, dispensed via a flow tube, to an additional port with flow through the anesthetic evaporator and hence an enrichment of the oxygen with anesthetic gas, usually by means of a mask or a nasal prong. The $O_2$ flush is a system arranged in parallel thereto, which can introduce an oxygen blast into the system by means of a button without flow through the anesthetic evaporator to flush anesthetic gases out of the respiration system.

Due to these four ways of dispensing being separately present in the system, the design effort for providing oxygen dispensing in three different ways and for also making available an oxygen blast as a possibility of dispensing in an additional, fourth way, is not insignificant.

SUMMARY OF THE INVENTION

An object of the present invention is therefore to provide a device at an anesthesia device, which makes it possible to combine the oxygen insufflation and emergency gas supply with one another.

Provisions are made according to the present invention for a switching element, which combines the oxygen insufflation unit in the anesthesia device with the emergency gas supply unit, to be present in an anesthesia device. Beginning from the oxygen feed in the anesthesia device, flow takes place through a flow tube with a control valve in a first embodiment according to the present invention. The quantity of oxygen then reaches the switching element. A first gas path for flow through an anesthetic evaporator with subsequent feeding of the oxygen to a patient is arranged at this switching element. Furthermore, a second gas path for routing the oxygen to a port for oxygen insufflation is arranged after the switching element. This first embodiment according to the present invention of a device for dispensing fresh gas, oxygen and anesthetic in an anesthesia device for connection to a patient comprises an anesthetic evaporator, an oxygen dispensing and display element, a switching element, a first gas path and a second gas path, a mixer with an oxygen port, with a nitrous oxide port and with an air port. The oxygen port is connected to an oxygen gas port of the device. Nitrous oxide, oxygen and air are mixed in the mixer. The mixed gas can reach the inlet of the anesthetic evaporator. The oxygen dispensing and display element is connected to the oxygen gas port and has an adjusting element for setting a rate of flow. The switching element is arranged downstream of the oxygen dispensing and display element. The first gas path and second gas path are arranged downstream of the switching element. The anesthetic evaporator is arranged in the first gas path and is designed to dispense anesthetic into the gas in the first gas path. The first gas path leads from the anesthetic evaporator to a connection and port element to the patient. The second gas path leads to a gas tapping port. The gas tapping port is provided for connecting a tube/tube-mask combination for oxygen insufflation. The switching element is designed such that sent oxygen, which is sent from the oxygen dispensing and display element arranged upstream, of the switching element to the switching element, is sent into the first gas path or into the second gas path. The oxygen reaches the connection and port element to the patient during flow through the first gas path after flowing through the anesthetic evaporator and is available at the gas tapping port during flow through the second gas path.

A detection element is arranged at the switching element in a preferred embodiment, which detection element is designed to detect the position, state and/or switching position of the switching element, to send it to a control unit for processing and, also preferably to display on a display unit whether the oxygen reaches the patient via the first gas path from the switching element through the anesthetic evaporator or whether the oxygen is sent via the second gas path to the port for oxygen insufflation.

In another preferred variant, the patient is connected to the device according to the present invention with the connection and port element via an inspiratory respiration tube and an inspiratory respiration tube. The oxygen now reaches the anesthetic evaporator via the first gas path, following the switching element, and from there the patient via the inspiratory respiration tube and via the connection and port element. The oxygen supplied to the patient is mixed more or less with anesthetic in case of feed via the first gas path, depending on the setting of the anesthetic evaporator.

In another preferred embodiment, the device for dispensing oxygen for an anesthesia device comprises an oxygen dispensing and display element and a switching element, wherein said switching element is arranged downstream of the oxygen dispensing and display element. The device for dispensing oxygen for an anesthesia device comprises, furthermore, a first gas path and a second gas path, wherein the first gas path and the second gas path are arranged downstream of the switching element, wherein an anesthetic evaporator is arranged in the first gas path and wherein a gas tapping port is arranged in the second gas path. The switching element is designed to send oxygen, which is sent from the oxygen dispensing and display element arranged upstream of the switching element to the switching element, into the first gas path or into the second gas path. During flow through the first gas path and flow through the anesthetic evaporator, the oxygen flows via a connection to the patient. During flow through the second gas path, the oxygen is available at the gas tapping port.

Provisions are made in a preferred embodiment for the switching element to send the oxygen either into the first gas path or into the second gas path without overlap. "Without overlap" means in terms of the present invention that no state in which gas can enter both the first gas path and the second gas path is possible.

In another preferred embodiment, the switching element is designed as a mechanical switching element, so that it is guaranteed that in case of the function as an emergency gas supply unit, the user is able at any time, without electric power, to deliver oxygen as a gas with evaporation of anesthetic to the patient via the flow tube and the first path. The mechanical switching element is also preferably designed for manual operation.

In this likewise preferred embodiment, the mechanical switching element is preferably designed as a ceramic disk valve. The ceramic disk valve is designed such that the oxygen is sent without overlap either into the first gas path for flowing through the anesthetic evaporator or into the second gas path to the port for the oxygen insufflation.

In another preferred embodiment, the switching element is designed as an electric, electromechanical, electropneumatic, electromagnetic or pneumatic or electropneumatic switching element, wherein the first gas path is set as the preferred position, so that the oxygen reaches the patient via the first gas path from the flow tube in a dispensed manner via the switching element through the anesthetic evaporator in case of failure of the power supply.

In an optional embodiment of the anesthesia device, an emergency/off or reset switching element is present, which enables the user to switch the device into a mode in which the emergency gas supply is used, i.e., this emergency gas supply can be triggered by this reset being actuated by the user at the switching element should an error occur in the rest of the anesthesia device, for example, in a mixer, which is normally operating, in which nitrous oxide, oxygen and air are mixed.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
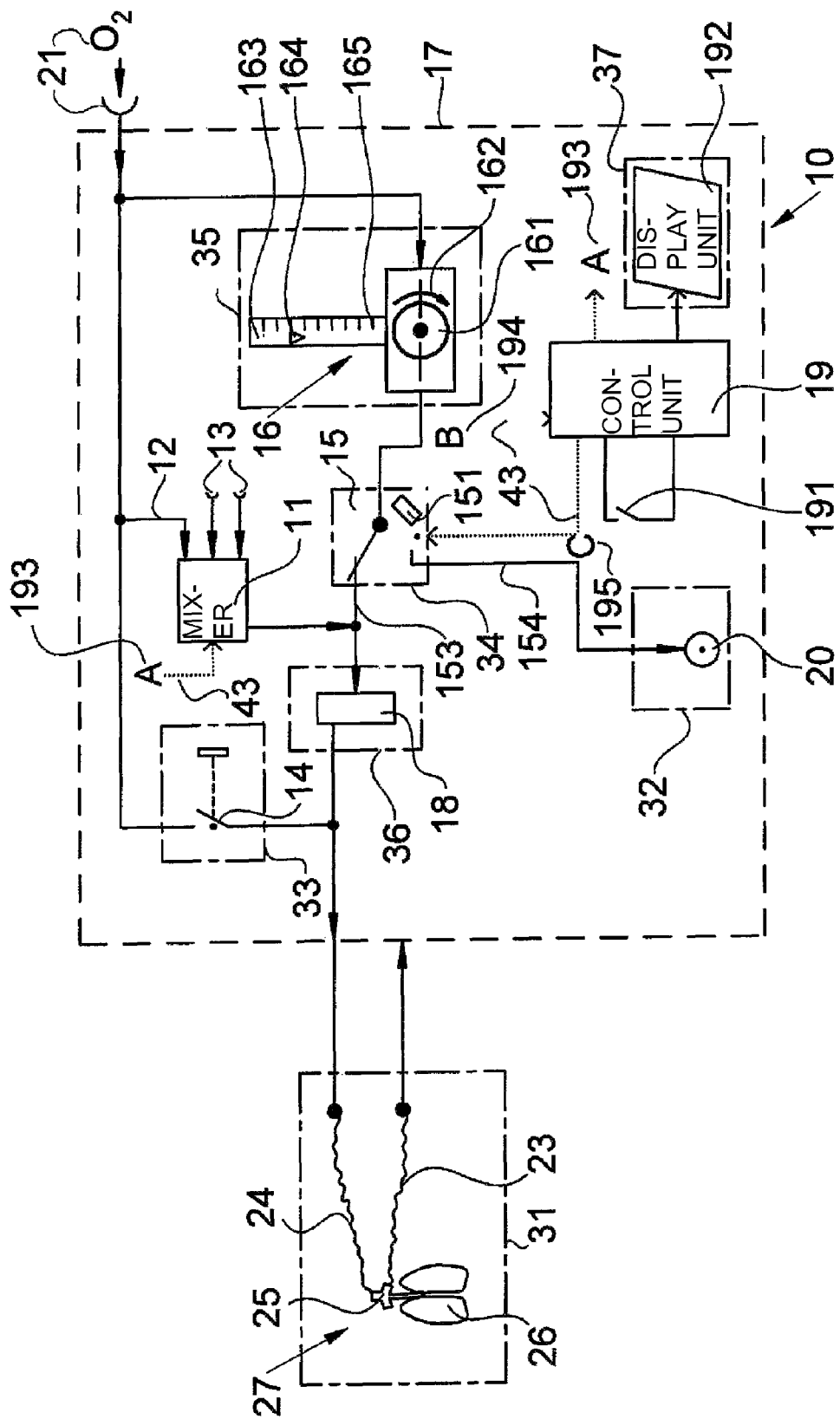
FIG. 1 is a schematic view showing a device according to the invention, as a part of an anesthesia device, for dispensing oxygen to the patient or to an oxygen insufflation port.

Referring to the drawings in particular, FIG. 1 shows a device for dispensing fresh gas, oxygen and anesthetic in an anesthesia device. This device 10 comprises as its elements a mixer 11, an oxygen port 12 at mixer 11, a nitrous oxide and air port 13 at mixer 11, an $O_2$ flush actuating and dispensing element 14, a switching element 15, a position detection element 151, an oxygen-dispensing and display element 16, an adjusting element 161, a flow tube 163, an anesthetic dispenser 18, a control unit 19, a shut-off element 191, a display unit 192, a gas tapping port 20, and an external $O_2$ gas port 21 as a gas inlet to the device 10. Gas-carrying connections between the elements of the device 10 are indicated by solid lines 40 in this FIG. 1, and electric connections 193, 194, 195 between the elements are indicated as dotted lines 43. Furthermore, FIG. 1 shows the patient 27 with his connections 23, 24, 25 to the anesthesia device. The device 10 for dispensing fresh gas, oxygen and anesthetic is connected to the patient 27 via an expiratory respiration tube 23 and an inspiratory respiration tube 24 as well as a connection and port element 25. Patient 27 is shown by means of a lung symbol 26. The oxygen-dispensing and display element 16 comprises a flow tube 163 and an adjusting element 161. A scale 165 is arranged at flow tube 163. A floating body 164 floats movingly up and down within the flow tube 163 behind the scale 165. The rate of flow through the oxygen-dispensing and display eminent 16 is adjusted and dispensed by the user by means of the adjusting element 161, which is adjustable along a direction of rotation and is closed and opened more or less by rotation in the corresponding direction of rotation 162. This makes it possible to adjust the flow in the oxygen-dispensing and display element 16 by means of the adjusting element 161 and the quantity of oxygen dispensed is displayed by means of the flow tube 163 and the floating body 164 and the scale 165. The oxygen is made available and distributed in the device 10 via the $O_2$ gas port 21. From the oxygen-dispensing and display element 16, the dispensed quantity of oxygen reaches the switching element 15. The dosed quantity of oxygen can be branched off from the switching element 15 into a first gas path 153 or into a second gas path 154 by switching or moving the switching element 15. The first gas path 153 then leads from the switching element 15 to the anesthetic dispenser 18 and from anesthetic dispenser 18 into the lungs 26 of patient 27 via the inspiratory respiration tube 24 and the connection and port element 25. The second gas path 154 leads from the switching element 15 to the gas tapping port 20. Gas tapping port 20 is set up and intended for connecting a tube/tube-mask combination for oxygen insufflation. Oxygen is also branched off from the $O_2$ gas port 21 leading to the device 10 via a parallel line to the $O_2$ flush actuating and dispensing element 14 and, likewise via a parallel line, to the oxygen port 12 at mixer 11. Gas, which includes the mixture of oxygen from the oxygen port 12 at mixer 11 and gases that are coupled in at the nitrous oxide and air port 13 of mixer 12, likewise reaches from mixer 11 the inlet of the anesthetic dispenser 18. In addition there is a branching off, in parallel to the oxygen that reaches mixer 11 or the oxygen-dispensing and display element 16, supplying $O_2$ directly to the $O_2$ flush actuating and dispensing element 14 and from there directly into the inspiratory respiration tube 24 to the patient 27 by means of the connection and port element 25. A position detection element 151 is optionally arranged at the switching element 15 in such a way as to recognize the position of the switching element 15, i.e., to recognize the selection of the gas path, i.e., to recognize whether oxygen is sent by the switching element 15 into the first gas path 153 or whether oxygen is sent into the second gas path 154. The position detection element 151 is connected to the control unit via a signal connection B 194. The control unit 19 analyzes this signal B from the position detection element 151 and sends it as information to a display unit 192. The user can then see on the display unit 192 the actual position of the switching element 15. A shut-off element 191 is provided at the control unit 19, and this shut-off element 191 makes it possible to send a signal to mixer 11 via a signal connection A 193 and to switch off this mixer, so that the device is put into a safe state, in which dispensing will take place exclusively via the oxygen-dispensing and display element 16 and the anesthetic dispenser 18 to patient 27.

In an alternative embodiment, switching element 15 is designed as an electrically and/or pneumatically actuated active switching element. The switching element 15 is actuated now via a functional connection C 195, which is led from the control unit 19 to the switching element 15. This active, electrically, electromechanically or pneumatically controlled switching element 15 is designed such that a preferred position is selected in case of failure of the power supply such that the gas flows through the switching element 15 in the direction of the first gas path 153 while flowing through the anesthetic dispenser 18 to the patient 27.

Besides the functional elements proper, the elements that are located outside the device 10 are integrated and shown in a group 31 in FIG. 1. A device boundary 17, indicated by broken line 41, encloses all elements with the device 10. The elements within the device 10, which are arranged and visible on the front side of the anesthesia device, are integrated in other groups 32, 33, 34, 35, 36, 37. Groups 31, 32, 33, 34, 35, 36, 37 are marked by dash-dotted lines. Groups 31, 32, 33, 34, 35, 36, 37 are explained in more detail in FIG. 2 and their arrangement on the front side of the anesthesia device is shown graphically and schematically according to FIG. 2.

Figure 2:
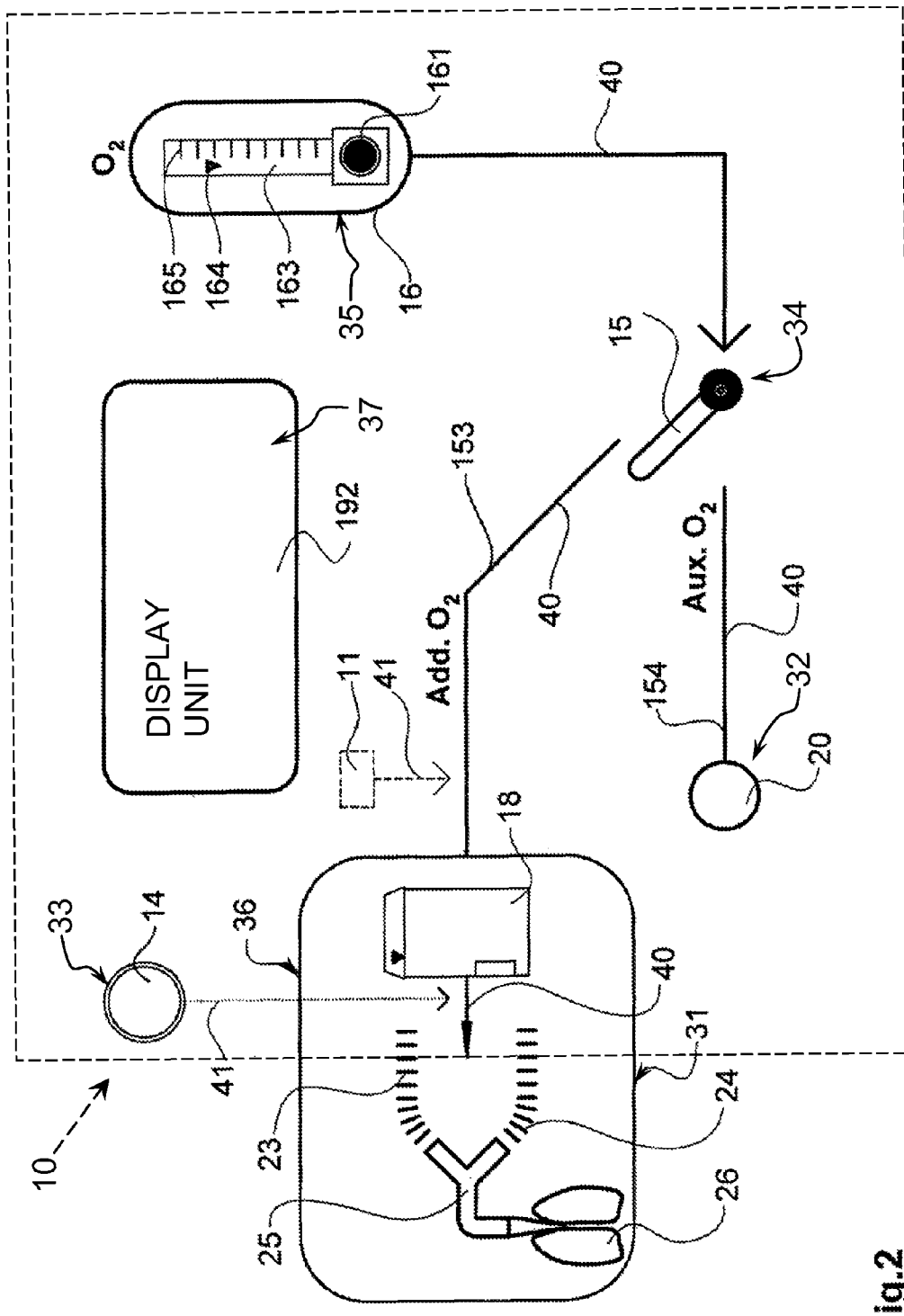
FIG. 2 is schematic view showing a device and a group of elements according to FIG. 1 on the front side of an anesthesia device.

FIG. 2 shows the device 10 according to FIG. 1 in a schematic, graphic form with the elements that are arranged and visible on the front side of an anesthesia device. Groups 31, 32, 33, 34, 35, 36, 37 in FIG. 2 correspond to groups 31, 32, 33, 34, 35, 36, 37 of the device 10 in FIG. 1. Identical elements in FIG. 2 are designated by the same reference numbers as the same elements and corresponding elements in FIG. 1. In a graphic representation, FIG. 2 schematically shows, in a simplified form, the switching element 15 for switching over between the first gas path 153 and the second gas path 154, the $O_2$ flush actuating and dispensing element 14, the oxygen-dispensing and display element 16, with adjusting element 161, flow tube 163, floating body 164 and scale 165 at the flow tube 163, as well as the display unit 192 and the gas tapping port 20 as elements of the groups of elements in the device, which are designated by 32, 33, 34, 35, 36, 37 according to the device 10 shown in FIG. 1 as a graphic representation on the front side of an anesthesia device. The connections in FIG. 2, to which the user has direct access on the front side, are shown by solid lines 40 in the graphic representation of a front side of the anesthesia device, to illustrate the interaction of the elements of device 10. The connections and elements shown by broken lines 41, for example, mixer 11, may be optionally shown additionally to illustrate the interaction of the elements of device 10. Group 31 shows in a graphic form the connection of device 10 to the patient 27 (FIG. 1) via the anesthetic evaporator 18, the inspiratory respiration tube 24 and via the connection and port element 25, which is typically designed as a so-called Y-piece, up into the lungs 26 of patient 27 (FIG. 1) and back into the device 10 via the expiratory respiration tube 23.

While specific embodiments of the invention have been shown and described in detail to illustrate the application of the principles of the invention, it will be understood that the invention may be embodied otherwise without departing from such principles.

APPENDIX

List of Reference Numbers

10 Device for dispensing fresh gas, oxygen and anesthetic
11 Mixer
12 Oxygen port at mixer
13 Nitrous oxide and air port at mixer
14 $O_2$ flush actuating and dispensing element
15 Switching element
151 Position detection element
153 First gas path
154 Second gas path
16 Oxygen-dispensing and display element
161 Adjusting element
162 Direction of rotation
163 Flow tube
164 Floating body
165 Scale
17 Device boundary
18 Anesthetic dispenser
19 Control unit
191 Shut-off element
192 Display unit
193 Signal connection A
194 Signal connection B
195 Functional connection C
20 Gas tapping port
21 External $O_2$ gas port leading to device
23 Expiratory respiration tube
24 Inspiratory respiration tube
25 Connection and port element
26 Lungs of a patient
27 Patient
31 Group of elements outside the device
32, 33, 34 Group of elements at device
35, 36, 37 Group of elements at device
40 Solid lines
41 Broken lines
42 Dash-dotted lines
43 Dotted lines

What is claimed is:

1. A dispensing device for dispensing fresh gas, oxygen and anesthetic in an anesthesia device for connection to a patient, the dispensing device comprising:
   an anesthetic evaporator with an inlet and an outlet;
   a device oxygen gas port;
   a mixer with an oxygen port, which is connected to said device oxygen gas port via a fluidic path branch, with a nitrous oxide port and with an air port, wherein nitrous oxide, oxygen and air are mixed in said mixer and wherein mixed gas can reach the inlet of the anesthetic evaporator;
   an oxygen-dispensing and display element, which is connected to said device oxygen gas port via another fluidic path branch and which has an adjusting element for adjusting a rate of flow and which displays the rate of flow;
   a switching element, wherein said switching element is arranged downstream of said oxygen-dispensing and display element;
   a gas tapping port provided for connecting a tube or tube and mask combination for oxygen insufflation;
   a connection and port element for the patient;
   a first gas path; and
   a second gas path, wherein said first gas path is arranged downstream of said switching element, said second gas path is arranged downstream of said switching element, said first gas path leads to the inlet of the anesthetic evaporator and from said anesthetic evaporator to said connection and port element for the patient, said second gas path leads to said gas tapping port, said switching element sending oxygen, which is sent from the oxygen-dispensing and display element arranged upstream of said switching element to said switching element, into said first gas path or into said second gas path, and oxygen reaches said connection and port element while flowing through said first gas path after flowing through said anesthetic evaporator and oxygen is available at said gas tapping port during flow through said second gas path, wherein:
   said switching element sends oxygen without overlap either into said first gas path or into said second gas path; and
   there is no state of the switching element in which oxygen simultaneously enters said first gas path and said second gas path.

2. A dispensing device in accordance with claim 1, wherein said switching element comprises a mechanical switching element.

3. A dispensing device in accordance with claim 2, wherein said switching element comprises a manually actuated mechanical switching element.

4. A dispensing device in accordance with claim 1, wherein said switching element comprises one of an electrical switching element, an electromagnetic switching element, an electromechanical switching element, a pneumatic switching element and an electropneumatic switching element.

5. A dispensing device in accordance with claim 1, further comprising detection means for at least one of:
   detecting a position of said switching element;
   detecting a state of said switching element; and
   detecting a switching position of said switching element.

6. A dispensing device in accordance with claim 5, further comprising:
   a control unit; and
   a display unit, wherein:
   said detection means is operatively connected to said control unit; and
   at least one of the position, the state and the switching position of said switching element are sent to said control unit for processing and/or are displayed on a display unit.

7. A dispensing device in accordance claim 1, further comprising a shut-off element for deactivating said mixer.

8. A dispensing device in accordance with claim 7, further comprising an energy supply, wherein:
   said switching element has a preferred position directing flow towards said first gas path; and
   said preferred position is brought about in a case of failure of said energy supply or by said shut-off element.

9. A dispensing device in accordance with claim 1, further comprising:
   an inspiratory respiration tube; and
   an expiratory respiration tube, wherein the dispensing device is connected to the patient via said connection and port element and via said inspiratory respiration tube and via said expiratory respiration tube.

10. A fresh gas, oxygen and anesthetic dispensing device for an anesthesia device, the dispenser dispensing device comprising:
    an anesthetic evaporator with an inlet and an outlet;
    a dispenser oxygen inlet port;
    a mixer with an oxygen inlet port operatively connected to said dispenser oxygen inlet port via a fluidic path branch, a nitrous oxide inlet port and an air inlet port, wherein nitrous oxide, oxygen and air are mixed in said mixer and the mixed gas is fed from the mixer to the inlet of the anesthetic evaporator;
    an oxygen-dispensing element connected to said dispenser oxygen inlet port via another fluidic path branch and having an adjusting element for adjusting a rate of flow and which displays the rate of flow;
    a switching element arranged downstream of said oxygen-dispensing element;
    a gas tapping port provided for connecting a tube or tube and mask combination for oxygen insufflation;
    a connection and port element for the patient;
    a first gas path; and
    a second gas path, said first gas path leading to the inlet of the anesthetic evaporator and said first gas path leading from said anesthetic evaporator to said connection and port element for the patient, said second gas path leading to said gas tapping port, said switching element sending oxygen, which is sent from the oxygen-dispensing element arranged upstream of said switching element to said switching element, either exclusively into said first gas path or exclusively into said second gas path, and oxygen reaches said connection and port element while flowing through said first gas path after flowing through said anesthetic evaporator and oxygen is available at said gas tapping port during flow through said second gas path, wherein said switching element does not send oxygen simultaneously into said first gas path and into said second gas path.

11. A dispensing device in accordance with claim 10, wherein said switching element comprises a mechanical switching element.

12. A dispensing device in accordance with claim 11, wherein said switching element comprises a manually actuated mechanical switching element.

13. A dispensing device in accordance with claim 10, wherein said switching element comprises one of an electrical switching element, an electromagnetic switching element, an electromechanical switching element, a pneumatic switching element and an electropneumatic switching element.

14. A dispensing device in accordance with claim 10, further comprising a position detector for at least one of:
- detecting a position of said switching element;
- detecting a state of said switching element; and
- detecting a switching position of said switching element.

15. A dispensing device in accordance with claim 14, further comprising:
- a control unit; and
- a display unit, wherein:
  - said position detector is operatively connected to said control unit; and
  - at least one of the position, the state, and the switching position of said switching element are sent to said control unit for processing and/or are displayed on a display unit.

16. A dispensing device in accordance claim 10, further comprising a shut-off element for deactivating said mixer.

17. A dispensing device in accordance with claim 16, further comprising an energy supply, wherein:
- said switching element has a preferred position directing flow towards said first gas path; and
- said preferred position is brought about in a case of failure of said energy supply or by said shut-off element.

18. A dispensing device in accordance with claim 10, further comprising:
- an inspiratory respiration tube; and
- an expiratory respiration tube, wherein the device is connected to the patient via said connection and port element and via said inspiratory respiration tube and via said expiratory respiration tube.

* * * * *